United States Patent [19]

Brockway

[11] Patent Number: 5,158,453
[45] Date of Patent: Oct. 27, 1992

[54] APPARATUS FOR SUPPORTING AND CONTROLLING FLUID DELIVERY TO A DENTAL HANDPIECE

[75] Inventor: Charles E. Brockway, Fairview, N.C.

[73] Assignee: Knight Manufacturing Inc., Asheville, N.C.

[21] Appl. No.: 834,606

[22] Filed: Feb. 12, 1992

[51] Int. Cl.⁵ ............................................. A61C 1/02
[52] U.S. Cl. ........................................ 433/28; 433/77
[58] Field of Search ................... 433/28, 77, 78, 84

[56] References Cited

U.S. PATENT DOCUMENTS

| | | | |
|---|---|---|---|
| 3,740,852 | 6/1973 | Holmqvist | 433/77 |
| 3,986,262 | 10/1976 | Casillas | 433/28 |
| 4,117,861 | 10/1978 | Betush | 433/28 |
| 4,375,963 | 3/1983 | Betush | 433/28 |

Primary Examiner—John J. Wilson
Attorney, Agent, or Firm—Shefte, Pinckney & Sawyer

[57] ABSTRACT

An apparatus for supporting and controlling fluid delivery to a dental handpiece includes a handpiece holding support arm pivotably mounted to a frame member with fluid-delivery tubing being affixed at spaced locations to the frame and to the support arm for folding of the tubing upon itself to close the tubing against fluid flow when the handpiece is mounted in the support arm's holder and for unfolding the tubing for open fluid flow when the handpiece is removed from the holder.

8 Claims, 4 Drawing Sheets

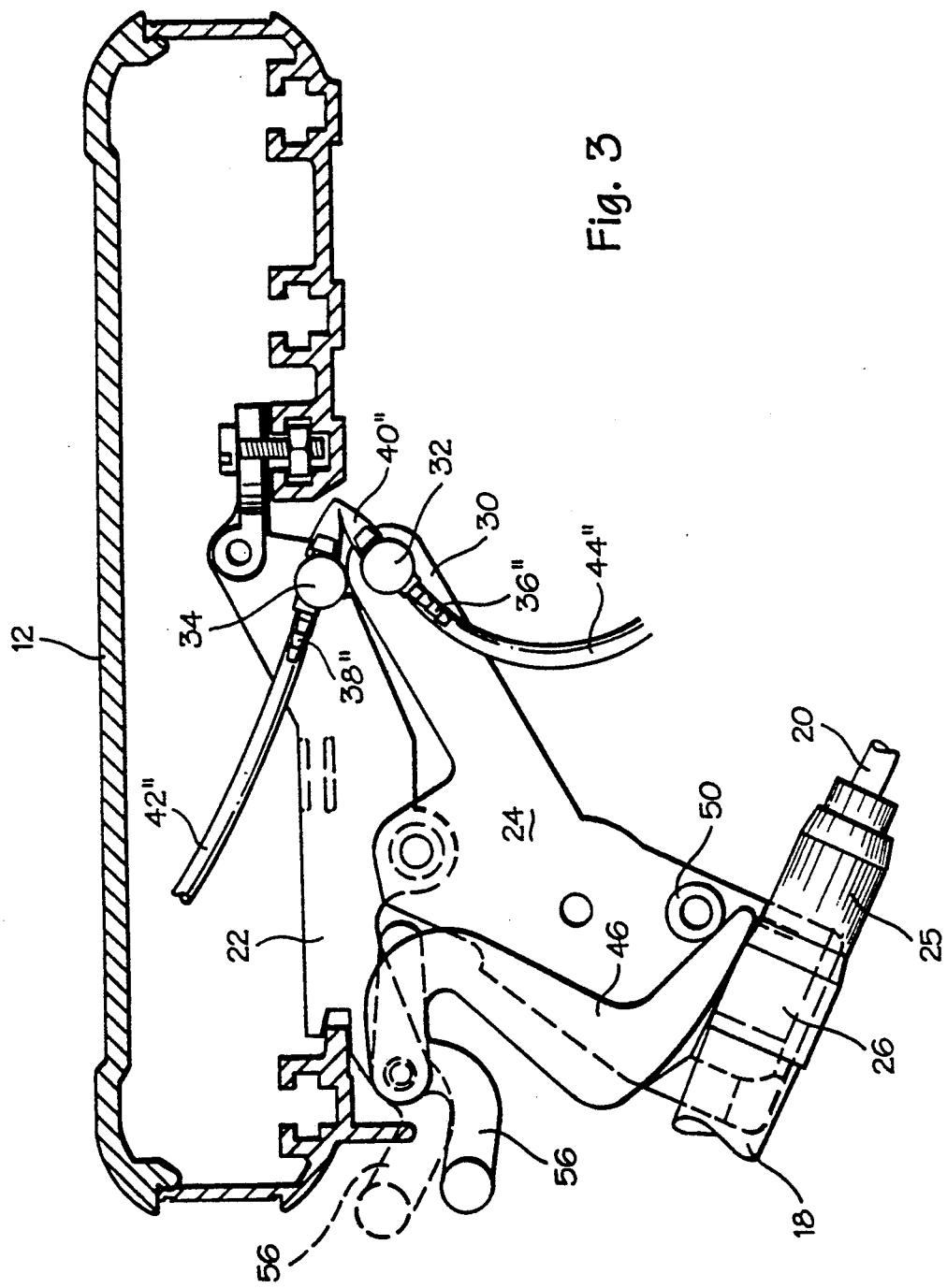

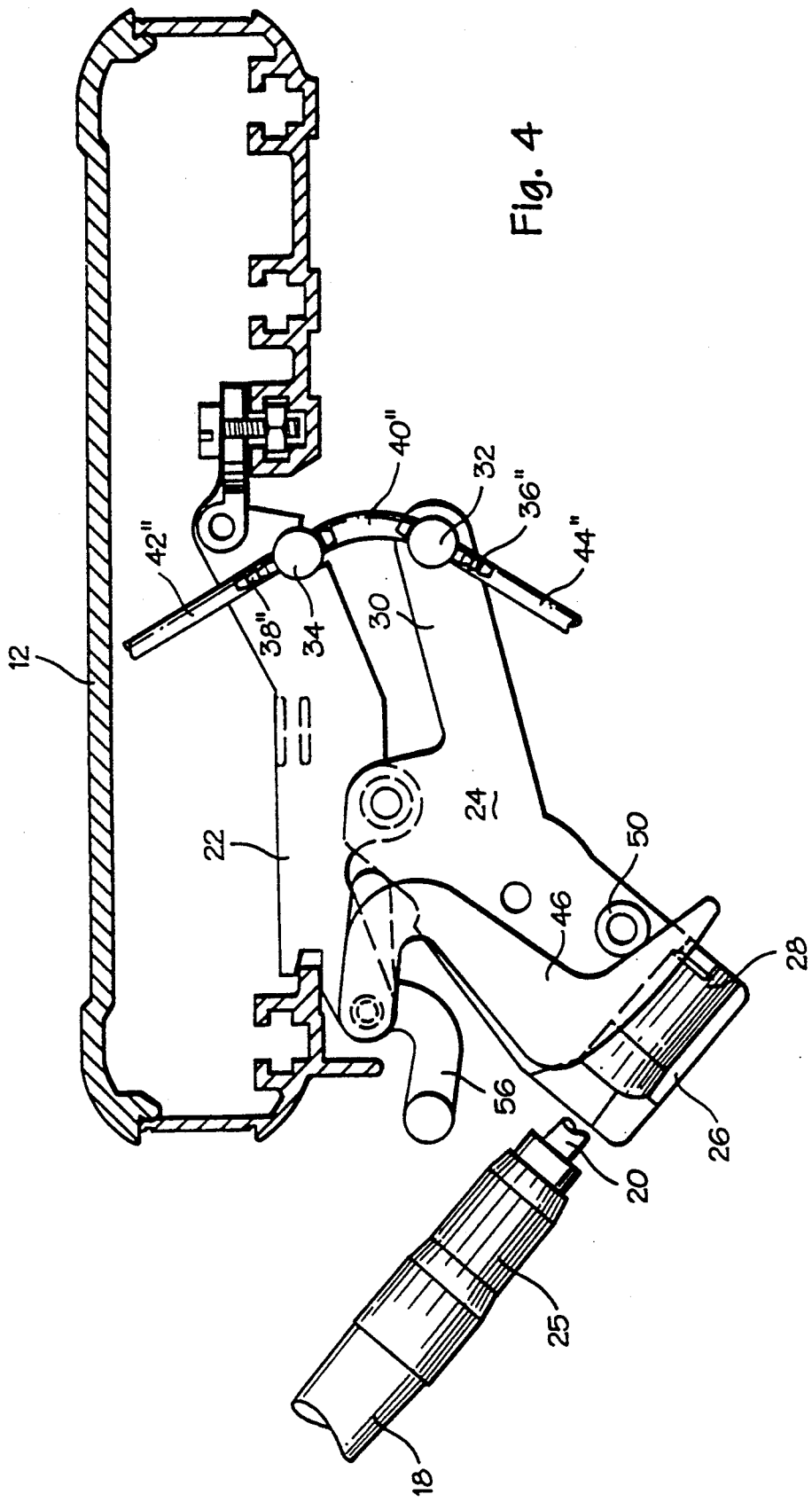

APPARATUS FOR SUPPORTING AND CONTROLLING FLUID DELIVERY TO A DENTAL HANDPIECE

BACKGROUND OF THE INVENTION

The present invention relates generally to dental office equipment of the type commonly used in dentist's offices for routine patient procedures. More particularly, the present invention relates to a novel apparatus for supporting and controlling delivery of fluids, such as air and water, to a dental handpiece, such as a dentist's drill.

Currently, conventional equipment used by practicing dentists typically comprises a variety of hand-held power-operated tools for performing differing dental procedures, one of the most common and familiar of which, by way of example, is a drill used for removing decayed portions of teeth preparatory to filling with a protective material. Typically, such drills and like dental handpieces are driven by compressed air and it is also commonplace for a cooling fluid, usually air, water or a mixture thereof, to be delivered to the handpiece for emission into the drilling or other work area for cooling purposes.

To facilitate convenient usage of such handpieces by dentists, a conduit system is provided in the dentist's office to provide a ready source of compressed air and pressurized water and is equipped with an associated valving system, normally actuated and deactuated through a foot-operated device, to enable the dentist to selectively control fluid delivery to the dental handpieces being utilized.

In the past, such valving systems have been relatively complicated and, in turn, costly, not only to manufacture but also to service when in need of repair. Accordingly, a need has existed for a simplified and less costly form of valve system for controlling delivery of operating fluids to dental handpieces.

U.S. Pat. No. 4,375,963, represents a relatively recent development addressing this problem and need. Basically, this patent discloses a control unit for dental handpieces wherein a handpiece holder is carried on a pivoting support arm mounted to a suitable frame member. A resiliently flexible tube is attached to the handpiece and extends therefrom through the frame member in a configuration tending to urge the support arm into an upwardly pivoted position when the handpiece is removed from the holder. An actuator is mounted in a stationary position on the frame member adjacent the holder for engagement by the handpiece when inserted into the holder to cause the support arm to pivot into a downward position. In such position, opposing pinch members mounted on the frame member and the support arm are moved into sufficiently close proximity to one another to physically clamp the flexible tube between the pinch members and thereby close the tube to prevent further fluid flow to the handpiece. Upon subsequent removal of the handpiece from the holder, the natural resiliency of the tube urges the support arm into its upward disposition, thereby separating the pinch members to allow fluid flow through the tube.

SUMMARY OF THE INVENTION

It is an object of the present invention to provide an equally simplified apparatus for supporting and controlling fluid delivery to a dental handpiece which avoids the necessity of physically pinching fluid delivery tubing to accomplish opening and closing thereof, but rather operates to close and open the tubing by folding and unfolding, i.e., kinking and unkinking, the tubing without physically contacting the tubing at the fold location.

Briefly summarized, the apparatus of the present invention, basically comprises a frame member, a support arm movably mounted to the frame member with a holder on the support arm for receiving a dental handpiece, and tubing for delivering a fluid to the dental handpiece. The tubing is affixed at spaced locations therealong respectively to the frame member and to the support arm to define a fixed length of the tubing therebetween. An actuator is associated with the support arm for causing the arm to move between a closed position when the handpiece is received by the support arm, wherein the fixed length of the tubing is folded upon itself to prevent fluid flow therethrough, and an open position when the handpiece is removed from the support arm, wherein the fixed length of the tubing is sufficiently relaxed to permit fluid flow therethrough.

In the preferred embodiment, the support arm is pivotably mounted to the frame member, with each of the frame member and the support arm rotatably supporting a respective tube connection pin to each of which the tubing is affixed to extend diametrically with respect to the pins at the spaced locations. In this manner, the tube connection pins move toward and away from one another upon movement of the support arm between its open and closed positions, during which the spaced locations on the tubing are permitted to rotate unitarily with the respective tube connection pins.

It is also preferred that the actuator be in the form of a cam member pivotably supported by the frame member to project into the holder for movement of the cam member in response to insertion and removal of the dental handpiece into and from the holder. A cam follower is mounted to the support arm in following relation to the cam member for transmitting movement of the cam member to the support arm.

According to another feature of the present invention, a latch is provided for selective operation to retain the support arm in its closed position irrespective of the receipt in or removal from the holder of the dental handpiece, the latch preferably being in the form of a lever movably mounted to the frame for movement into and out of locking engagement with the support arm.

BRIEF DESCRIPTION OF THE DRAWINGS

FIG. 3 is a vertical cross-sectional view of the dental handpiece supporting and controlling apparatus of FIG. 2, taken along line 3—3 thereof, showing the support arm in its closed position with the dental handpiece received in the holder; and FIG. 4 is another cross-sectional view similar to FIG. 3, showing the support arm in its open position with the dental handpiece removed from the holder.

DESCRIPTION OF THE PREFERRED EMBODIMENT

Figure 1:
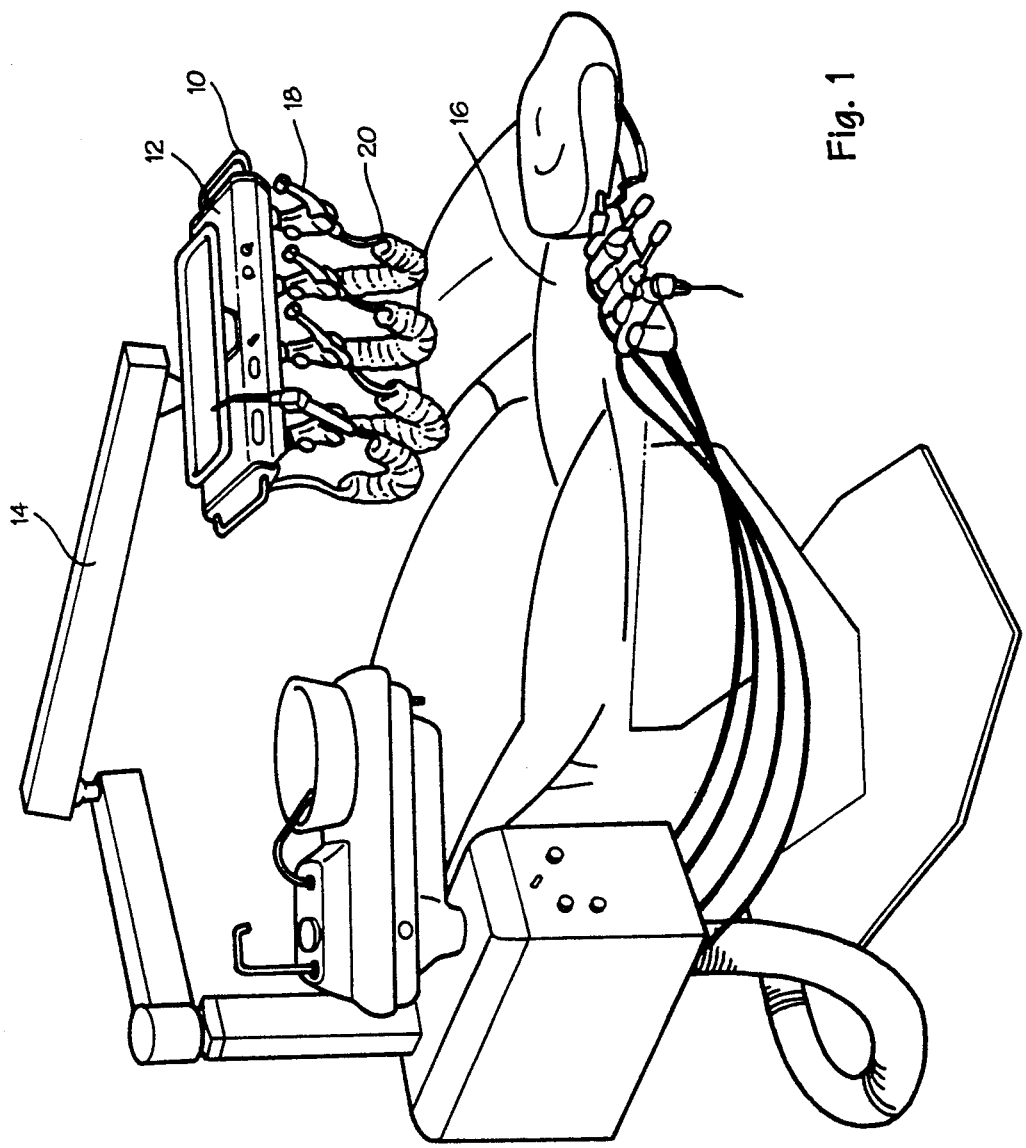
FIG. 1 is a perspective view of a typical dental chair structure including an instrument head assembly on which a plurality of dental handpieces are mounted by a support and control apparatus according to the preferred embodiment of the present invention.

Referring now to the accompanying drawings and initially to FIG. 1, a plurality of dental handpiece supporting and controlling apparatus units according to the present invention are shown generally at 10 as preferably embodied in an instrument head 12 mounted on an articulated support linkage 14 in association with a conventional dental chair 16. Each apparatus unit 10 is operative to support an individual respective dental handpiece 18, e.g., a dental drill, and to control delivery of operating fluids, e.g., pressurized air and water, to the respective handpiece 18 through appropriate tubing, shown only at 20 in FIG. 1. The apparatus 10 of the present invention is particularly adapted for use with conventional dental handpieces 18 of the type designed to be powered by pressurized air and also supplied with a pressurized cooling fluid such as water, air or both. By way of example but without limitation, the apparatus of the present invention is described herein as preferably embodied for supporting and controlling a conventional dental drill, wherein the exposed drill bit is operatively connected interiorly with a turbine configured to be rotatably driven by a supply of compressed air delivered through the tubing 20 and wherein separate supplies of coolant water and air are also delivered through the tubing 20 for emission from the drill at the drilling location for cooling purposes, as more fully explained hereinafter. However, those persons skilled in the art will readily recognize that the apparatus of the present invention is equally applicable for supporting and controlling any other form of dental handpiece wherein at least one operating fluid is to be selectively supplied to the handpiece during use.

Figure 2:
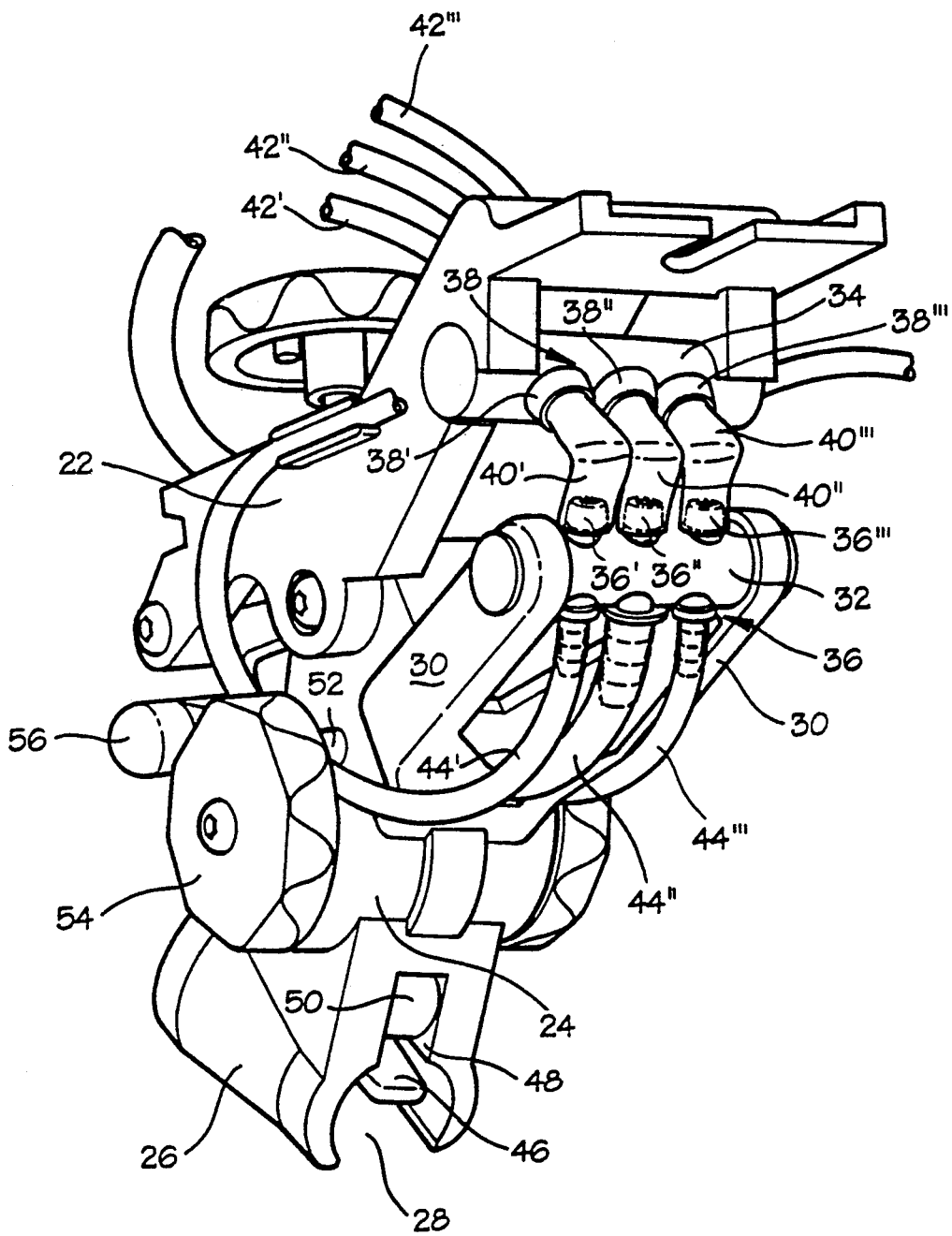
FIG. 2 is a perspective view of one dental handpiece supporting and controlling apparatus of FIG. 1.

As best seen in FIG. 2, each dental handpiece supporting and controlling apparatus unit 10 includes a bracket-like frame member 22 rigidly affixed to the underside of the instrument head 12. An elongated support arm 24 is pivotably mounted generally centrally along its length to the underside of the frame member 22, with the forward end of the support arm 24 being configured in the form of a saddle at 26 defining a forwardly opening channel 28 adapted to serve as a handpiece holder for selective insertion and removal of the respective handpiece 18 into and out of the channel 28. To facilitate a secure fitted receipt of a handpiece 18 within the channel 28 of the saddle-shaped holder 26, the base of the handpiece 18 is fitted with an adapter nut 25 whose outer peripheral shape conforms closely to the interior dimensions and configuration of the holder channel 28.

The opposite end of the support arm 24 is formed with a pair of laterally spaced forks 30 between which a pin 28 is rotatably supported in parallel relation to the pivot axis of the support arm 24. A corresponding pin 34 is similarly mounted rotatably to the underside of the frame member 22 adjacent and in parallel relation to the pin 32. Each of the pins 32,34 are formed with three corresponding diametrical bores, each bore having a respective tubular fitting 36,38 secured therein to project outwardly from each opposite side of the respective pin 32,34. Each corresponding pair of fittings 36',38'; 36'',38''; 36''',38''', are communicated with one another by a segment of a resiliently flexible tube 40',40'',40''', respectively, each tube segment being of the same fixed predetermined length with its opposite ends respectively connected to the associated pair of fittings 36',38'; 36'',38''; 36''',38'''. The opposite end of each fitting 38',38'',38''' secured to the pin 34 of the frame member 22 is connected to a corresponding supply tube 42',42'',42''', which extend from the respective apparatus 10 through the instrument head 12 and the articulated support linkage 14 to suitable sources of fluid supply (not shown). Specifically, the supply tube 42' is connected to a source of coolant water under pressure and the supply tube 42''' is connected to a source of coolant air under pressure, while the supply tube 42'' is connected to another source of pressurized air to provide a motive force for driving the operating components of the associated handpiece 18, e.g., the turbine of a dental drill. The opposite ends of the fittings 36',36'',36''' secured to the pin 32 on the support arm 24 are connected with respective delivery tubes 44',44'',44''' for delivery of the respective pressurized fluids to the associated handpiece 18, the delivery tube 44'' being operatively connected to the handpiece 18 to deliver pressurized air to the handpiece turbine or other drive components while the delivery tubes 44',44''' are connected to the handpiece 18 to deliver cooling air and water for emission in the region of handpiece operation, as previously indicated.

As will be recognized by those persons skilled in the art, it is also possible in appropriate dental chair arrangements to connect the supply tubes to the fittings 36 and to connect the delivery tubes to the fittings 38 according to the particular tubing arrangement, without departing from the scope or substance of the present invention. Thus, it is to be understood that the particular tubing arrangement as hereinabove described and as illustrated in the accompanying drawings is only for purposes of illustration and explanation of this invention which is not to be so limited.

The saddle-like handpiece holder portion 26 of the support arm 24 is formed with a central longitudinally-extending slot 48 within which is disposed an actuator cam 46 of a generally Z-shape, one end of the actuator cam 46 being pivotably mounted to the frame member 22 at a location forwardly of the pivot mounting location of the support arm 24 with the opposite end of the actuator cam 46 extending within the slot 48 linearly along the channel 28. A cam follower roller 50 is rotatably supported by the holder portion 26 of the support arm 24 within the slot 48 for following engagement with the adjacent surface of the actuator cam 46 which faces inwardly of the slot 48.

Normal operation of the handpiece supporting and controlling apparatus 10 of the present invention may thus be understood with reference to FIGS. 3 and 4. When the handpiece 18 is inserted fully into the channel 28 of the holder 26, the adapter nut 25 on the base of the handpiece 18 engages the free end of the actuator cam 46 to pivot it counterclockwise (as viewed in FIGS. 3 and 4) into a position fully retracted within the slot 48. This pivotal movement of the actuator cam 46 is transmitted to the cam follower roller 50 causing the support arm 24 to correspondingly pivot counterclockwise into a closed position, shown in FIG. 3, wherein the tube connection pin 32 at the opposite forked end of the support arm 24 is held in sufficiently close proximity to the tube connection pin 34 on the frame member 22 to cause the tube segments 40',40'',40''' to become folded upon themselves into a crimped or kinked configuration sufficient to block fluid flow through the tube segments. Thus, with the handpiece 18 supported within the holder 26, fluid flow through the tube system of the apparatus 10 is prevented, regardless of actuation of the foot controls by the dentist. Upon removal of the handpiece 18 from the holder 26, the natural resiliency of the flexible tube segments 40',40",40"' acts through the fittings 36,38 to pivot the support arm 24 and the cam actuator 46 in a clockwise direction while simultaneously rotating the tube connection pins 32,34 into an open position of the apparatus 10, shown in FIG. 4, wherein the tube segments 40',40",40"' are sufficiently unfolded to permit fluid flow therethrough. Thus, upon actuation by the dentist of the associated foot-operated control with the handpiece supporting and controlling apparatus 10 in this open position, pressurized operating fluid, i.e., air, water or both, is permitted to flow through the tubing system to the handpiece 18 for normal operation thereof.

As best seen in FIG. 2, an intermediate portion along the length of each delivery tube 44',44",44"' is directed between a respective pinch pin 52 and an associated eccentric control wheel 54 to enable the dentist to individually pinch each delivery tube to selected varying degrees as determined by the rotational disposition of the eccentric control wheels 54 relative to the pinch pins 52. In this manner, fine adjustments may be made in the maximum rate of fluid flow through the respective supply and delivery tubes. In addition, the control wheels 54 permit any one or more of the supply tubes 42',42",42"' to be completely closed, irrespective of the disposition of the support arm 24 in the open or closed positions of FIGS. 3 and 4.

The present apparatus 10 is additionally equipped with a latching lever 56 pivotably mounted to the frame member 22 coaxially with the actuator cam 46 for selective movement between an inoperative disposition, shown in full lines in FIG. 3, wherein the lever 56 permits normal operative movements of the support arm 24 between the open and closed positions, and a latching disposition shown in broken lines in FIG. 3, wherein the lever 56 is pivoted into engagement with the support arm 24 to prevent movement thereof into the open position irrespective of whether the handpiece 18 is supported in or removed from the holder 26.

Those persons skilled in the art will readily recognize that the dental handpiece supporting and controlling apparatus 10 of the present invention is of a simplified construction which is relatively inexpensive to produce and furthermore should operate reliably over a relatively extended useful life.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. Apparatus for supporting and controlling fluid delivery to a dental handpiece, said apparatus comprising a frame member, a support arm movably mounted to said frame member, said support arm having a holder for receiving the dental handpiece, tube means for delivering a fluid to the dental handpiece, said tube means being affixed at spaced locations therealong respectively to said frame member and to said support arm to define a fixed length of said tube means therebetween, and actuator means associated with said support arm for causing said support arm to move between a closed position when the handpiece is received by said support arm wherein said fixed length of said tube means is folded upon itself to prevent fluid flow therethrough and an open position when the handpiece is removed from said support arm wherein said fixed length of said tube means is sufficiently relaxed to permit fluid flow therethrough.

2. Apparatus for supporting and controlling fluid delivery to a dental handpiece according to claim 1, wherein said support arm is arranged to move said spaced locations of affixation of said tube means toward and away from one another upon movement of said support arm between said open and closed positions.

3. Apparatus for supporting and controlling fluid delivery to a dental handpiece according to claim 2, wherein said support arm is pivotably mounted to said frame member.

4. Apparatus for supporting and controlling fluid delivery to a dental handpiece according to claim 2, wherein said frame member rotatably supports a first tube connection pin and said support arm rotatably supports a second tube connection pin, said tube means being affixed to said tube connection pins in diametrical relation thereto at said spaced locations along said tube means for unitary rotational movement of said tube connection pins and said tube means upon movement of said support arm.

5. Apparatus for supporting and controlling fluid delivery to a dental handpiece according to claim 1, wherein said actuator means comprises a cam member movably supported by said frame member and projecting into said holder for movement of said cam member in response to insertion and removal of the dental handpiece into and from said holder.

6. Apparatus for supporting and controlling fluid delivery to a dental handpiece according to claim 5, wherein a cam follower is mounted to said support arm in following relation to said cam member for transmitting movement of said cam member to said support arm.

7. Apparatus for supporting and controlling fluid delivery to a dental handpiece according to claim 1, and characterized further by latch means selectively operable for retaining said support arm in said closed position irrespective of the receipt in or removal from said holder of the dental handpiece.

8. Apparatus for supporting and controlling fluid delivery to a dental handpiece according to claim 7, wherein said latch means comprises a lever movably mounted to said frame for movement into and out of locking engagement with said support arm.

* * * * *